US00PP14553P29

(12) United States Plant Patent
Kaagman

(10) Patent No.: US PP14,553 P2
(45) Date of Patent: Feb. 17, 2004

(54) DAHLIA PLANT NAMED 'DADA SCARLET'

(50) Latin Name: *Dahlia variabilis*
Varietal Denomination: Dada Scarlet

(75) Inventor: Pim Kaagman, Andijk (NL)

(73) Assignee: Goldsmith seeds, Inc., Gilroy, CA (US)

( * ) Notice: Subject to any disclaimer, the term of this patent is extended or adjusted under 35 U.S.C. 154(b) by 0 days.

(21) Appl. No.: 10/404,827

(22) Filed: Apr. 1, 2003

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—A. Para
(74) *Attorney, Agent, or Firm*—Jondle & Associates PC

(57) ABSTRACT

A dahlia cultivar particularly distinguished by red colored flowers, compact habit and good basal branching.

1 Drawing Sheet

Genus and species: *Dahlia variabilis.*
Variety denomination: 'Dada Scarlet'.

BACKGROUND OF THE NEW PLANT

The present invention comprises a new and distinct cultivar of dahlia, botanically known as *Dahlia variabilis*, and hereinafter referred to by the cultivar name 'Dada Scarlet'. The new cultivar is asexually reproduced from vegetative cuttings and tissue culture resulting from the cross of the seed/pod parent Dahlstar Red, a unpatented commercial line×DL-111-7, a deep purple proprietary line that is unnamed and unpatented.

'Dada Scarlet' is a product of a planned breeding program intended to create new dahlia plants with red colored flowers, compact habit, good basal branching and moderately vigorous growth.

The new cultivar was created in 1997 in Andijk, The Netherlands and has been asexually reproduced repeatedly by vegetative cuttings and tissue culture in Gilroy, Calif., Andijk, The Netherlands, and Guatemala over a four-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature inflorescence.

DESCRIPTION OF THE NEW CULTIVAR

The following detailed descriptions set forth the distinctive characteristics of 'Dada Scarlet'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings taken. Color references are primarily to The R.H.S Colour Chart of The Royal Horticultural Society of London (R.H.S.). Texture description details were observed under a dissecting microscope according to The New Royal Horticultural Society Dictionary of Gardening (1992).

Classification:
- *Botanical.*—*Dahlia varabilis.*
- *Commercial.*—Dahlia.

Growth:
- *Form.*—Upright, compact and mounding.
- *Growth and branching habit.*—Good vigorous habit, well branched, full plant.
- *Height.*—From soil level to top of blooms: Approximately 25–30 cm.
- *Width.*—Approximately 35–40 cm including flowers.
- *Time to produce a finished flowering plant.*—9–12 weeks.
- *Outdoor plant performance.*—Fast cropping, free flowering, used in patio planters and mixed container plantings or garden beds.
- *Time to initiate roots.*—Approximately 14–28 days in the greenhouse.
- *Root description.*—Fibrous, white.

Leaves:
- *Arrangement.*—Young foliage leaves are single and mature leaves simple or occasionally compound and trifoliate, opposite.
- *Length.*—5.0–6.0 cm.
- *Width.*—3.5–4.0 cm.
- *Leaf blade shape.*—Elliptic to Ovate.
- *Leaf margin.*—Dentate/Ciliate.
- *Apex aspect.*—Caudate.
- *Base aspect.*—Attenuate.
- *Leaf color.*—Upper surface, closest to RHS 147A (yellow-green) but a little lighter green and Undersurface, RHS 191A (greyed-green) base color, with RHS# 137B (green) veining.
- *Texture.*—Occasional hispid with strigulose on veins.
- *Venation.*—Pinnate.
- *Venation color.*—RHS 144B (yellow-green).
- *Petiole length.*—2.0–2.3 cm.
- *Petiole width.*—0.2–0.3 cm.
- *Petiole color.*—RHS 144B (yellow-green).
- *Petiole texture.*—Occasional hispid and strigulose.

Stem:

*Length.*—25–30 cm.

*Diameter.*—0.4–0.5 cm.

*Internodes length.*—0.5–0.7 cm.

*Color.*—RHS 144A (yellow-green) but a little lighter.

*Texture.*—Occasional hispid.

*Stem anthocyanin.*—No.

*Peduncle color.*—RHS 144A (yellow-green).

*Peduncle length.*—2.0–2.2 cm.

*Peduncle diameter.*—0.2 cm.

*Peduncle texture.*—Smooth.

*Peduncle anthocyanin.*—Showing in irregular patches.

Bud:

*Shape.*—Orbicular.

*Diameter.*—0.7–1.0 cm.

*Length.*—0.6–1.0 cm.

*Color at tight bud.*—RHS 46A (red) when bracts divide.

Flower:

*Blooming habit.*—Continuous all through the growing season. Good floriferousness.

*Inflorescence type.*—Borne on terminals above foliage, semi-double flowers, floret faces upward or outward.

*Flower diameter.*—3.5–4.2 cm.

*Ray petal color.*—Front side, RHS 44A (red) and Underside, RHS 44C (red) base color with RHS 19C (yellow-orange) faint streaks. Petal length — 1.5–1.65 cm. Petal width — 0.9–1.0 cm. Petal apex shape — Semi-praemorse. Petal base shape — Spathulate. Petal margin — Entire. Petal texture — Papillose. Petal quantity — 38–45.

*Disc petal color.*—RHS 5A (yellow). Petal length — 0.7 cm. Petal diameter — 0.15–0.2 cm. Petal shape — Elongated, cylindrical, shiny. Petal quantity — 30–38.

*Involucral bracts.*—Usually 5, sometimes up to 7 or 8.

*Color.*—RHS 191B (greyed-green) base color with RHS 189A (greyed-green) veining.

*Length.*—0.7–0.8 cm.

*Width.*—0.3 cm.

*Shape.*—Ovate.

*Apex.*—Acute.

*Texture.*—Strigulose on upper side, basally.

*Lastingness of individual blooms.*—7–12 days.

*Fragrance.*—No.

Reproductive organs:

*Androecium, pollen color.*—RHS# 5A (yellow).

*Gynoecium, stigma color.*—RHS# 4A (yellow).

*Style color.*—RHS 4B (yellow).

*Pistil length.*—0.9 cm.

*Fruit seed set.*—Not observed.

Disease and insect resistance: Not observed.

COMPARISON WITH KNOWN CULTIVARS

'Dada Scarlet' differs from the female parent 'Dahlstar Red' in the following ways: 'Dada Scarlet' has a lighter color and is more compact and shorter peduncles than Dahlstar Red.

'Dada Scarlet' differs from the male parent DL-111-7 in the following ways: 'Dada Scarlet' has smaller flowers and is compact and the male is a regular size plant and flower.

I claim:

1. A new and distinct dahlia plant as shown and described herein.

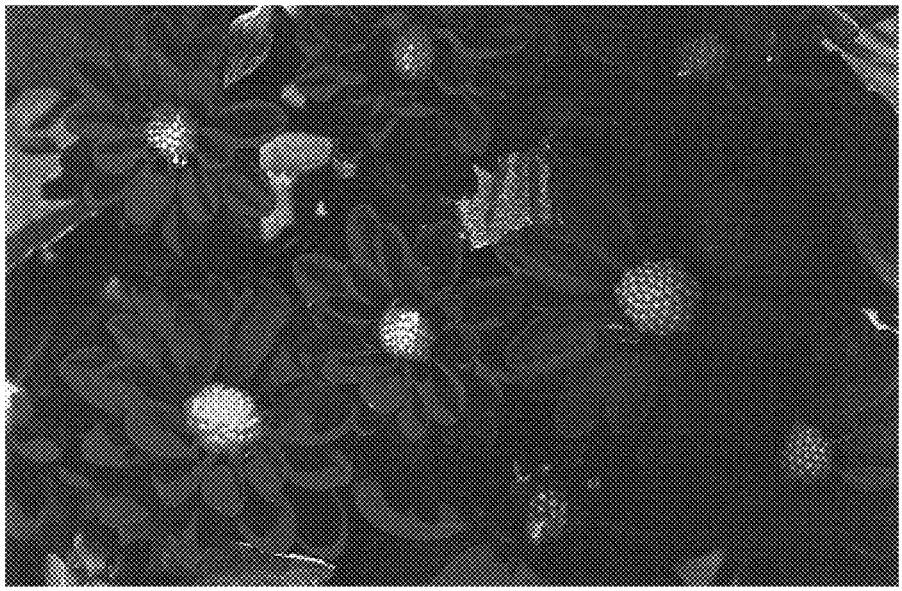

* * * * *